(12) United States Patent
Hussam et al.

(10) Patent No.: US 11,488,691 B2
(45) Date of Patent: Nov. 1, 2022

(54) MEDICAL REGISTRIES

(71) Applicant: Universal Research Solutions, LLC, Columbia, MO (US)

(72) Inventors: Ali Adel Hussam, Columbia, MO (US); Nathan Bleigh, Kansas City, MO (US)

(73) Assignee: Universal Research Solutions, LLC, Columbia, MO (US)

( * ) Notice: Subject to any disclaimer, the term of this patent is extended or adjusted under 35 U.S.C. 154(b) by 674 days.

(21) Appl. No.: 14/569,245

(22) Filed: Dec. 12, 2014

(65) Prior Publication Data

US 2016/0171163 A1    Jun. 16, 2016

(51) Int. Cl.
*G16H 10/60* (2018.01)
*G16H 70/00* (2018.01)

(52) U.S. Cl.
CPC .......... *G16H 10/60* (2018.01); *G16H 70/00* (2018.01)

(58) Field of Classification Search
CPC ..... H04L 63/10; H04L 67/306; H04L 63/102; H04L 67/02; H04L 63/20; H04L 9/40; H04L 63/101; H04L 63/105
USPC .......................................... 705/2, 3
See application file for complete search history.

(56) References Cited

U.S. PATENT DOCUMENTS

| | | | | |
|---|---|---|---|---|
| 6,151,581 A * | 11/2000 | Kraftson | ............... | G06Q 10/10 705/3 |
| 2006/0041450 A1* | 2/2006 | Dugan | ............... | G16H 40/67 705/2 |
| 2008/0215370 A1* | 9/2008 | Dent | ............... | G06F 21/6245 705/3 |
| 2013/0197941 A1* | 8/2013 | Cochran | ............... | G16H 10/65 705/3 |
| 2014/0316812 A1* | 10/2014 | Hathorn | ............... | G16H 10/60 705/3 |

OTHER PUBLICATIONS

S. L. Ting, "A Clinical Decision Support System for Medical Prescription Process." Order No. 3500893, Hong Kong Polytechnic University (Hong Kong), Ann Arbor, 2011. (Year: 2011).*

Y. Zhang, "An Access Control and Trust Management Framework for Loosely-Coupled Multidomain Environments." Order No. 3471932, University of Pittsburgh, Ann Arbor, 2010. (Year: 2010).*

* cited by examiner

*Primary Examiner* — Rachel L. Porter
(74) *Attorney, Agent, or Firm* — Fish & Richardson P.C.

(57) ABSTRACT

A computer-implemented includes integrating a practice management system with a medical registry system that includes a medical registry for storing medical information; receiving, through an automated feed with the practice management system, information indicative of patients of a medical facility associated with the practice management system; updating the medical registry with the information indicative of the patients; assigning a plurality of medical forms to the patients; transmitting the assigned medical forms to client devices of the patients; receiving, through the automated feed with the practice management system, answers to questions included in the medical forms; updating database records in the medical registry with the answers to the medical forms; and tracking, based on the updated database records, compliance metrics for completion of the medical forms.

18 Claims, 10 Drawing Sheets

MEDICAL REGISTRIES

BACKGROUND

Medical forms are used to collect data and information regarding a patient's symptoms and conditions. One technique for preparing a medical form is to manually edit a pre-existing form (e.g., a form existing in Microsoft Word™ format) with new or customized questions. The form is then sent to review boards for review through a physical or electronic mailing. Additionally, once a form has been finalized, it may be presented to a patient, study participant or other individual (collectively referred to as "patients" herein, without limitation, for purposes of convenience). For example, physicians may present patients with the forms when the patient visits the physician's office. Additionally, hardcopy (i.e., paper) versions of medical forms may be distributed to patients for completion. For patient's who have not completed medical forms prior to the patient's examination, the patient may often complete the medical form at the physician's office by filling out a hardcopy of the form.

Frequently, the patient's responses to the questions included in the medical forms are entered into a computerized system by medical personnel. In this case, in order for a physician to review the patient's responses, the physician may access the computerized system and view the answers to the questions, which is often a lengthy process of reviewing individual questions.

SUMMARY

In one aspect of the present disclosure, a computer-implemented method includes integrating a practice management system with a medical registry system that includes a medical registry for storing medical information; receiving, through an automated feed with the practice management system, information indicative of patients of a medical facility associated with the practice management system; updating, by a server system comprising at least one processor on a network, the medical registry with the information indicative of the patients; assigning by the server system a plurality of medical forms to the patients; transmitting the assigned medical forms to client devices of the patients; receiving, through the automated feed with the practice management system, answers to questions included in the medical forms; updating database records in the medical registry with the answers to the medical forms; tracking, based on the updated database records, compliance metrics for completion of the medical forms. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The actions include generating, in the medical registry, a plurality of sub-registries for storing the answers, with a sub-registry being for a particular type of medical information and with access of the sub-registry being limited to users who have submitted to the sub-registry the particular type of medical information. A first one of the sub-registries is an orthopedics sub-registry, and a second one of the sub-registries is a cardiology sub-registry. The actions include storing information indicative of an identity of a user who submitted the answers. The actions include receiving, from a client device, a request to access information in one of the sub-registries; determining a type of medical information stored in the requested sub-registry; determining whether a user associated the client device has contributed to the requested sub-registry the determined type of medical information; when the user has not contributed to the requested sub-registry the determined type of medical information, denying access to the sub-registry; and when the user has contributed to the requested sub-registry the determined type of medical information, granting access to the sub-registry. The medical registry is a first medical registry for storage of a first type of medical information, wherein at least one of the transmitted medical forms is a condensed version of medical forms that condenses a set questions included in the medical forms into a subset of questions in a single form, and wherein the method further comprises: accessing a plurality of medical registries, with the plurality of medical registries including the first medical registry and with each of the plurality of medical registries being dedicated to storage of a particular type of information; filtering the answers to the questions to determine which answers are relevant to which medical registries; and using answers from the condensed medical form to populate the plurality of medical registries by assigning, based on filtering, the answers to one or more of the medical registries in the plurality; wherein at least one of the answers is assigned to two or more of the medical registries. The actions include automatically scoring multiple patient-reporting outcomes with a condensed version of a medical form, based on the answers that are received via the automated feed.

All or part of the foregoing may be implemented as a computer program product including instructions that are stored on one or more non-transitory machine-readable storage media (or one or more machine-readable hardware storage devices), and that are executable on one or more processing devices. All or part of the foregoing may be implemented as an apparatus, method, or electronic system that may include one or more processing devices and memory to store executable instructions to implement the stated functions.

The details of one or more implementations are set forth in the accompanying drawings and the description below. Other features, objects, and advantages will be apparent from the description and drawings, and from the claims.

DETAILED DESCRIPTION

Described herein is a system for generating a medical registry, e.g., using information collected through various medical forms. Generally, a medical registry includes a repository (e.g., data repository) for medical information and data that is made available and/or viewable. To facilitate searching of the medical registry, information is often input into the medical in a specified format, e.g., according to data specifications. For example, a medical database may require that a search query or search term have a specified number of letters and/or numerals and/or have a pre-fix. In this example, the system formats the information that is input into the medical registry by adding the pre-fix and/or the requisite letters/numerals.

To additionally facilitate searching, a medical registry is segmented into various areas, e.g., to allow a user to search a specific area. For example, the various areas may be based on medical specialties and/or areas of medicine. There may be a cardiology area (e.g., for storage of cardiology information), an implants area (e.g., for storage of information indicative of medical implants), an outcomes area (e.g., for storage of information indicative of medical outcomes of various medical procedures and treatments), and so forth.

Figure 1:
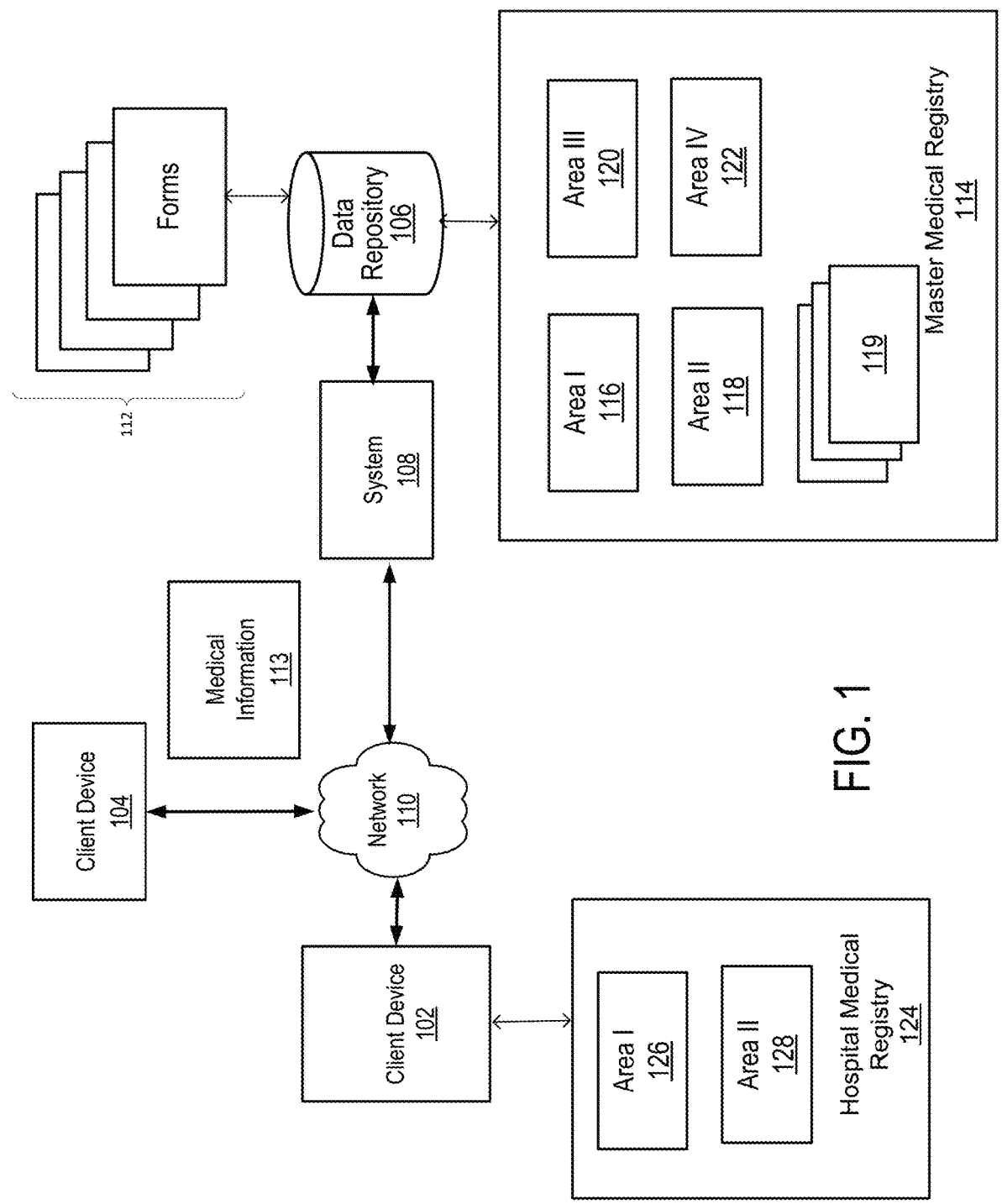
FIG. 1 is a diagram of a system that implements a medical registry.

Referring to FIG. 1, networked environment 100 includes client devices 102, 104, data repository 106, system 108 and network 110. In this example, system 108 builds and maintains master medical registry 114 with medical information that is received from various and numerous client devices, including, e.g., client devices 102, 104. In this example, master medical registry 114 is stored in data repository 106. Master medical registry 114 includes areas 116, 118, 120, 122 for storage of particular types of information. System 108 stores forms 112 in data repository 106. In this example, forms 112 include various types of medical forms with questions for collecting information. In an example, a medical form is specific to a particular service provider and is accessible to patients of that service provider. In another example, a medical form is accessible to patients who satisfy pre-specified criteria, e.g., such as possessing a particular medical problem.

In the example, of FIG. 1, system 108 sends one or more of forms 112 to client devices 102, 104. In response, one or more of client devices 102, 104 send medical information 113 (via an automated and automatic data feed that is preconfigured to interface between system 108 and client device 104 and/or client device 102) to system 108. In this example, medical information 113 includes medical information that is received from one or more entities (e.g., medical offices, electronic medical record (EMR) systems, hospitals, and so forth). In this example, medical information 113 includes answers to questions included in forms 112. System 108 parses and analyzes medical information 113 and stores/updates master medical registry 114 with the medical information 113 (e.g., after formatting medical information 113 as needed). In an example, a medical registry is updated by inserting information into a database record to transform the database record.

In the example of FIG. 1, system 108 stores medical information 113 in areas 116, 118, 120, 122 of master medical registry 114. There are various ways in which system 108 determines which of areas 116, 118, 120, 122 to store various portions of medical information 113. In an example, medical information 113 includes answers to series of questions. In this example, each answer is associated with metadata (in medical information 113) that specifies an area for the answer (e.g., via an area code). In this example, each of areas 116, 118, 120, 122 is also associated with an area code. System 108 stores portions of medical information 113 in one or more of areas 116, 118, 120, 122 based on matching area codes (between the portion and one or more of areas 116, 118, 120, 122).

Client device 102 (e.g., a client device associated with a hospital) also implements its own medical registry 124 (e.g., with medical information that is collected from users associated with the hospital and who are completing one or more of forms 112). In this example, medical registry 124 also includes various areas 126, 128 for storage of various types of information. Client device 102 determines which area of medical registry 124 to store medical information, using various techniques, including those previously described.

Repository 108 also includes electronic records 119 (database records). In an example, an area of medical registry 114 is comprised of records 119. Data repository 106 and/or system 108 transforms electronic records 119 by inserting medical information 113 to generate formatted data records. Data repository 106 returns the formatted data records to system 108 to enable retrieval of information from the sub-registry.

Figure 2:
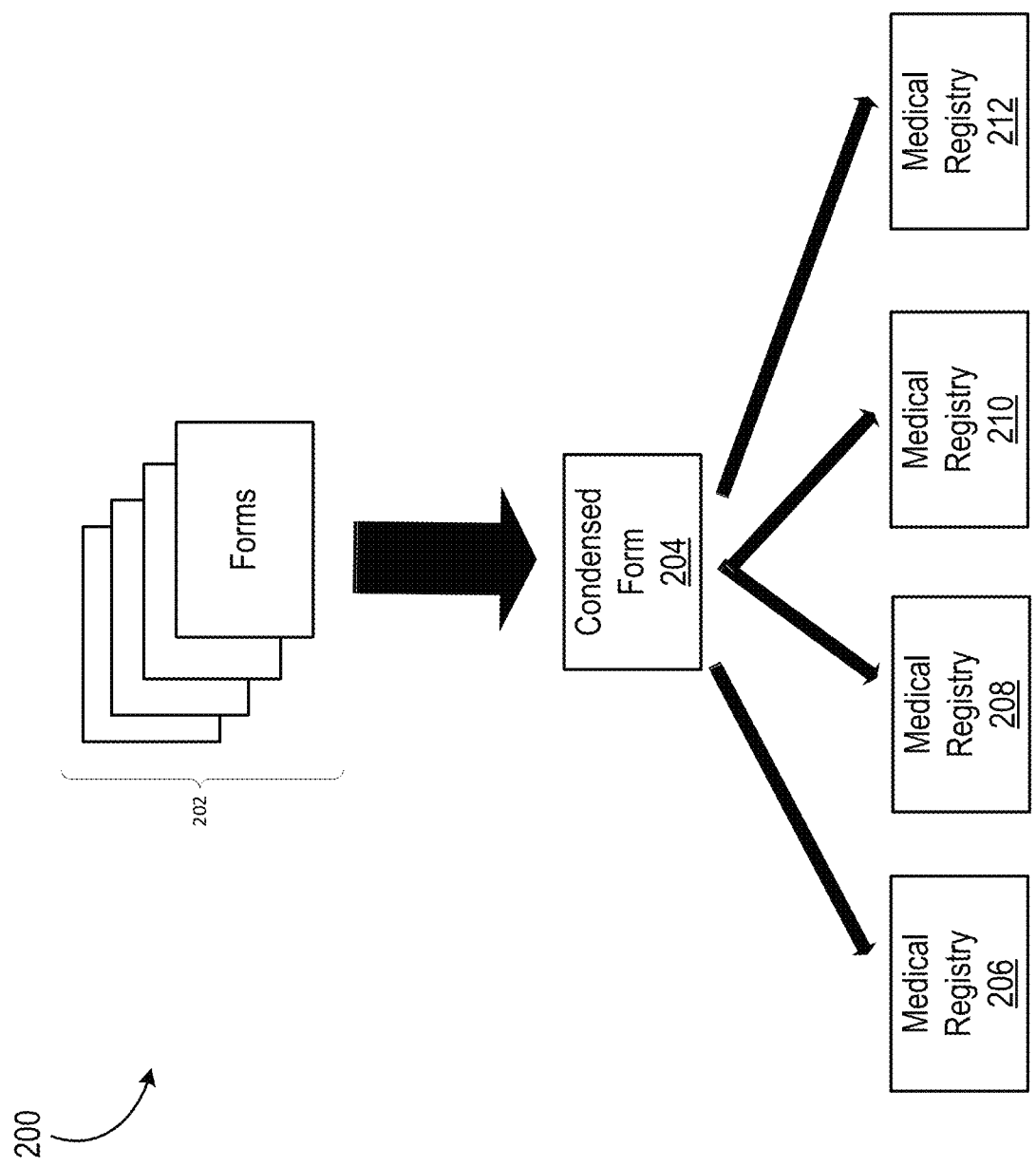
FIG. 2 is diagram of using a condensed form for population of a medical registry.

Referring to FIG. 2, diagram 200 displays a visualization of using a condensed form 204 to populated numerous, different medical registries 206, 208, 210, 212 (e.g., registries associated with different entities or different registries associated with a same entity). In this example, condensed form 204 is a condensed version of forms 202. Forms 202 include one or more same or similar questions. Generally, similar questions are questions with a threshold amount of similarity. In an example, the system determines when two questions are similar by detecting same and/or similar words among the questions (e.g., by detecting a predefined, threshold amount of same or similar words). In this example, a system condenses similar questions by selecting one of the questions for presentation and/or by merging the questions together into a single question. The system merges the questions together by assessing the meaning of the various questions and generating a new question that incorporates the various meanings A module for condensing similar questions is described in U.S. Pat. No. 8,429,547, the contents of which are incorporated herein by reference.

In this example, a system (e.g., system 108) uses answers received from the condensed form 204 and other contents from condensed form 204 to populate medical registries 206, 208, 210, 212. In an example, medical registries 206, 208, 210, 212 are associated with different facilities (e.g., hospitals) and/or there may be different medical registries for different areas of medicine. For example, medical registry 206 may be for outcomes and medical registry 208 may be for demographics data. Through condensed form 204, system 108 populates medical registries with increased efficiency, relative to the efficiency of populating the medical registry from multiple, uncondensed forms. In an example, it is more efficient to populate a medical registry from a condensed form, because system 108 only needs to parse contents of a single form, i.e., the condensed form.

In still another example, system 108 accesses a plurality of medical registries, with the plurality of medical registries including the first medical registry and with each of the plurality of medical registries being dedicated to storage of a particular type of information. System 108 also receives answers to questions included in a condensed questionnaire, e.g., a questionnaire that condenses questions from a plurality of forms—for example, by providing a subset of the questions. System 108 filters the answers to the questions to determine which answers are relevant to which medical registries. There are various ways in which system 108 filters, including, e.g., by using the content of the answers to determine a subject matter and then determining a correspondence between the determined subject matter and subject matter designations for the various sub-registries. System 108 also uses answers from the condensed medical form to populate the plurality of medical registries by assigning, based on filtering, the answers to one or more of the medical registries in the plurality, with at least one of the answers being assigned to two or more of the medical registries.

Figure 3:
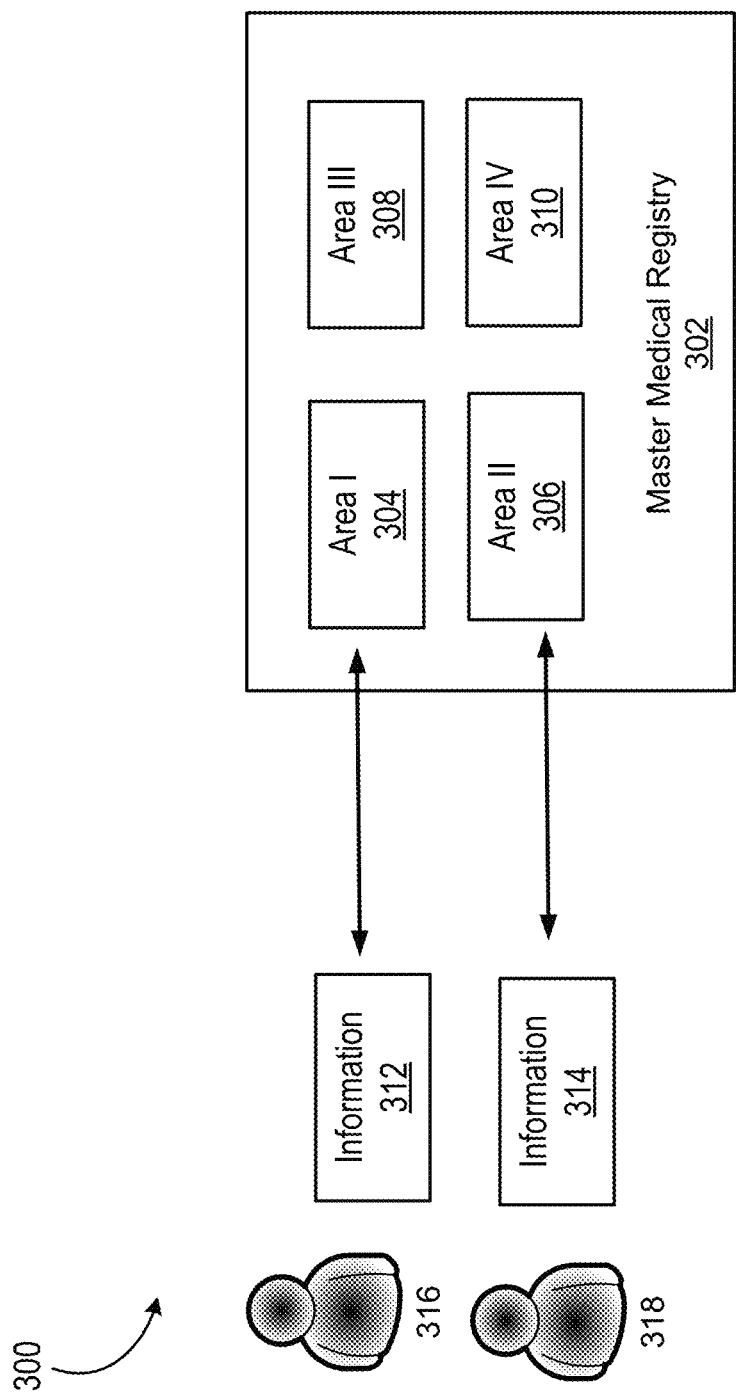
FIG. 3 is a diagram of permission restrictions for accessing information in a medical registry.

Referring to FIG. 3, diagram 300 illustrates that in some examples users are restricted to accessing, from a master medical registry 302, only those areas in which the user contributes. In this example, master medical registry 302 includes areas 304, 306, 308, 310. In this example, user 316 submits information 312 (in area I and/or a type that is associated with area I) to master medical registry 302. Because user 316 has submitted information that pertains to area I, user 316 is able to access area 304 in master medical registry 302, but is restricted (unable) to access other areas. User 318 submits information 314 (in area II and/or a type that is associated with area II) to master medical registry 302. Because user 318 has submitted information that pertains to area II, user 318 is able to access area 306 in master medical registry 302, but is restricted (unable) to access other areas (with other types of information that don't match the type of information submitted by user 318).

Using the techniques described herein, the registries leverage a data collection and compliance monitoring system (e.g., system 108) to generate accurate and meaningful registries without burdening the participants. The system does this in many ways. For example, the system's condensing operations allow for multiple patient-reporting outcomes to be scored, without having the patient fill an overwhelming numbers of questions. Additionally, physicians using the system have access to compliance monitoring (e.g., in which the system monitors whether patients have complied with the requirements of various forms (by completing the forms) and reminding those patients who have not yet completed the forms), which increases patient participation. Additionally, physicians using the system improve their workflow as the system automatically releases forms to patients and sends reminders. These responses are then auto-fed to the registry. Furthermore, the system is configured to interface with a bar scanner to receive implant information, e.g., to allow physicians to input implant information into a medical registry.

In an example, various registries have various different levels of flexibility. Because not every registry has the same needs and goals, the system provides different models of registries, each with varying levels of required data, setups, and features. The system is also configured for automation of data procurement and feeding to the registry, as the registry is designed to be as minimally invasive as possible to a physician's current workflow. As such, once a physician's office or hospital joins the registry, the system automatically releases forms to patients, sends reminders to patients, and feeds this data to the registry. Various types of registries are described below.

Figure 4:
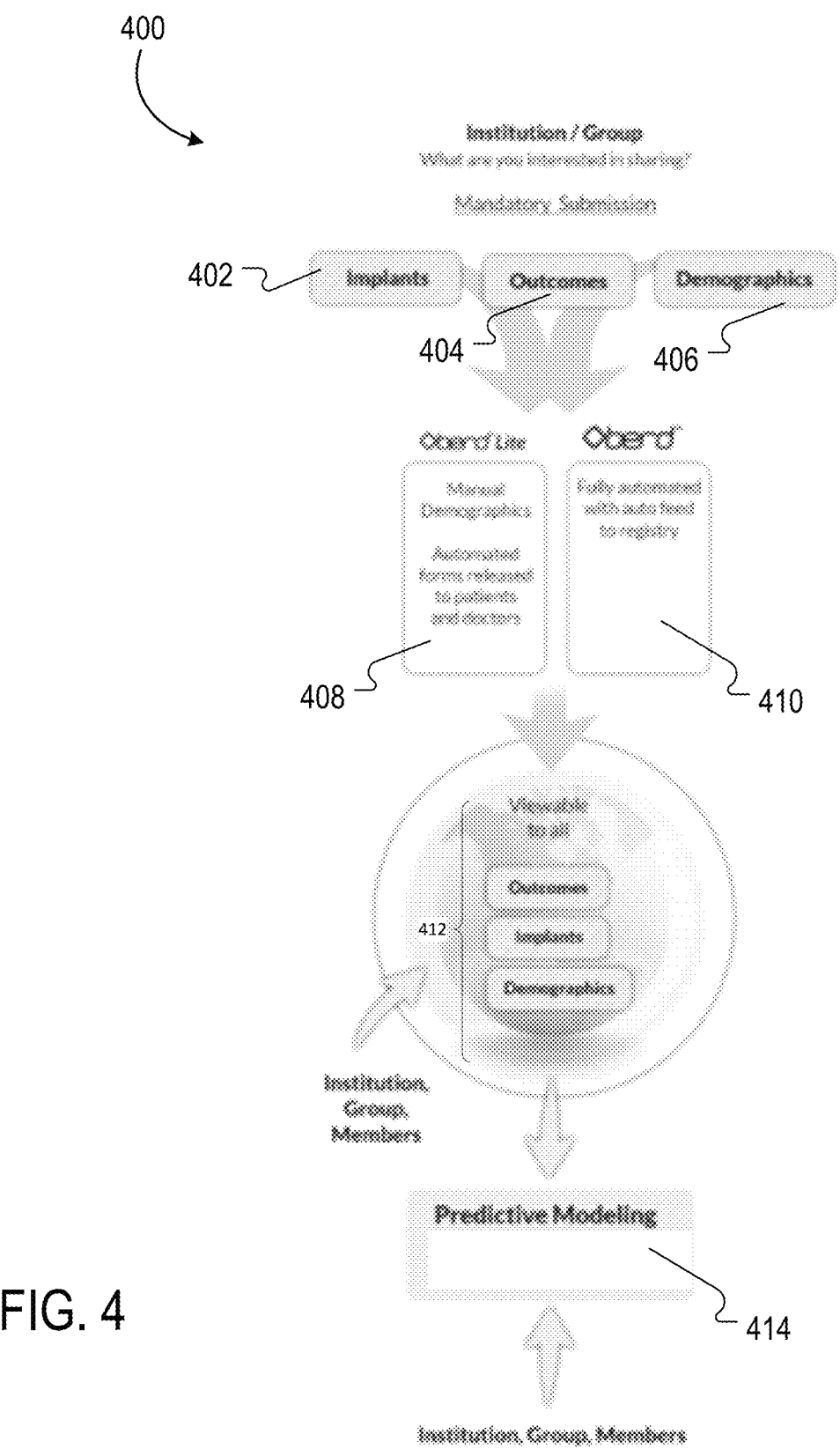
FIGS. 4-6 are diagrams of implementations of various medical registries.

Referring to FIG. 4, diagram 400 illustrates a process flow for a particular type of registry. The registry 412 requires the setting of standards for submission of implants data 402, outcomes data 404, and demographics data 406. Additionally, the system is accessible to registered and/or licensed users of the system (e.g., system 408 and/or system 410). In some example, system 108 is system 410. As shown in FIG. 4, medical registry data is available to all users (e.g., in de-identified form).

In an example, the system is configured for integration with the individual or group's practice management system for full automation of patient data filling into the system (e.g., when the individual or group has a license for the system). The system is configured for full automation of forms being sent to the patient participants and auto feeding to the registry database. In another example, the system is configured for automation of forms to patient participants and auto feeding to the registry database (e.g., via a Lite license). This option is independent of an interface between the system and a practice management system, which requires manual entry of patient participants into the system.

Standards for patient-reported outcomes (PROs), implants, and other data points are set by the registry administrators and are required for submissions. Throughout the data collection process, participants are granted real-time access to the de-identified database (e.g., a medical registry in which patient identifying information such as a name, age, address, social security number and so forth is removed). Participants also have access to the system's data mining module, which includes statistical functions, graphing, and export to CSV, and access to a raw export tool. In an example, the system includes predictive modeling component 414, which uses statistical methods to predict, or forecast trends to identify patients that are at risk based on the PROs and other collected data points.

In this example of FIG. 4, submission of implants, outcomes, and demographics data is mandatory, e.g., for participation in the medical registry. A registry board determines standards for the various types of data that is stored in the registry. In addition to the required type of data, a user may also submit, other types of data.

In an example, the system (e.g., system 108) establishes a connection (e.g., a virtual private network connection) with a client device (that implements an institution/group practice management system) and is used to pass scheduling (SIU) and patient demographics (ADT) messages from the institution/group practice management system to system 108. System 108 automates the collection of PROs on preset timelines. Physicians can scan or key in implants data directly into system 108. In this example, system 108 will work with the implants company to create a pre-populated list of implants that is included in within an operative form. All collected information is auto fed to the registry database. Registry data can be accessed in real-time through the Oberd data-mining module or through a full export of the data.

In another example, submission of information is independent of an interface existing between system 108 and the institution/group practice management system. In this example, patient demographic and surgery dates are manually entered into the system. Following the manual entry of patient demographics, the full automation of the system is available, including, e.g., the reporting and data retrieval. PROs are sent at preset time intervals. Implants data input is automated through the preset list of implants. Data is auto fed to the registry database, with real-time access to data-mining module and the export tool.

The registry board will select which demographic data must be included in the registry database (for example age, gender, race, weight, height, etc.). One type of demographic data is comorbidities data and information indicative of Complex Chronic Disease (CCD). In this example, an external client device sends an electronic medical record (EMR) to system 108 and system 108 can parse the EMR for a CCD to include in the registry. Additionally, the system uses a form to collect desired demographic data, if the requirements exceed age, gender, race, and ethnicity.

The medical registry also collects patient-reported outcomes (PROs) data. A patient-reported outcome or PRO is a questionnaire used in a clinical trial or a clinical setting, where the responses are collected directly from the patient. The system determines a discrete list of PROs that will be assigned to all patients included in the registry. For example, a shoulder registry may select the Simple Shoulder Test (SST), American Shoulder Elbow Society (ASES), and a Single Assessment Numeric Evaluation (SANE) as the PROs. In this example, all participates in the registry must release all selected PROs to all patients included in the particular registry.

In another example, not all PROs are in system 108 (and/or in the accompanying database). For new PRO requests, the system will follow the following protocol. The system determines if any licensing or copyright requirements exist to use the PRO. If there are no copyright/licensing requirements, the system will input the form exactly as displayed in the provided copy or the most official version. The system will apply a scoring algorithm to results of the PRO, e.g., to assess the effectiveness of certain medical procedures and/or devices. If there are copyright/licensing requirements, the system contacts the authors of the PRO to determine the requirements of the copyright/licensing. If there are costs assessed for the use of the PRO within the system, the system will determine internally if that cost will be passed to the users of the registry.

The most commonly used PRO questionnaires assess one of the following attributes: symptoms (impairments) and other aspects of well-being, functioning (disability), health status, general health perceptions, health related quality of life (HRQoL) and reports and Ratings of health care. Measures of symptoms may focus on a range of impairments or on a specific impairment such as depression or pain. Measures of functioning assess activities such as personal care, activities of daily living and locomotor activities. Health-related quality of life instruments are generally multi-dimensional questionnaires assessing a combination of aspects of impairments and/or disability and reflect a patient's health status. In contrast, QoL goes beyond impairment and disability by asking about the patient's ability to fulfill their needs and also about their emotional response to their restrictions. In an example, a patient is prompted to rate (e.g., select a value for) each attribute in the PRO questionnaire. System 108 then scores the PRO questionnaire by aggregating the selected value. This provides a score for an outcome of a particular medical procedure and/or an outcome of a particular medical device.

System 108 also implements a questionnaire timeline. The system determines the time points at with the patient will complete their PROs prior to and following their surgery. For example, the registry may determine to collect PROs at the follow time points: pre-op, 6 weeks, 3 months, 6 months, 1 year, 2 years, 3 years, 4 years, 5 years. The time points will be locked for the registry and all patient included in the registry will receive the PROs at those time points.

The system allows for customization of the amount of time in which a patient has to fill their PRO at each time point. For example, the patient may be given the full length of time between the scheduling of their surgery and until the day of surgery to fill their PROs for the "pre-op" time point. For the 6 week time point, the patient could be given 2 weeks to complete the assigned PROs.

System 108 is also configured to collect implant data, e.g., by scanning a barcode included on an implant to send to system 108 information indicative of the implant and/or when the implant is being delivered. In an example, a registry board determines a list of implants to be included in the study. The registry board provides a contact at the implants company to assist the system in the creation of an implants data list (that promotes scanning of barcodes). The implants form will be generated in the system where the implants data will be entered along with any other operative information required for the registry.

System 108 also supports participation (in the registry) by invitation only and requires the participant to be a licensed user.

System 108 performs data collection to populate a registry, e.g., based on patient consent. In an example, system 108 collects demographics information from an external system (e.g., a patient management system at a hospital) and/or from manual uploading and/or form receipt of medical history forms and electronic medical records (EMRs).

System 108 is also configured for automation of PROs. In this example, system 108 implements a release of forms. Patient-reported outcomes will be automatically assigned and sent electronically to patients according to the release timeline created during the registry setup. The release timeline is set according to a "surgical date" and then uses the surgery date of each patient to accurately assign the forms. System also implements patient reminders. As PROs are assigned and available for a patient to fill, based on the registry release timeline, patients will receive an email from system 108 reminding the patient. The email will indicate patient's agreement to participate in the study, instructions on how to access the forms, a link to a patient portal of system 108.

In this example, system 108 implements a patient portal for accessing and viewing patient form. The patient can access the patient portal through the secure link provided in the email reminder or through a link that the institution provides upon scheduling the surgery or includes on their website. If the patient accesses the patient portal through the secure email link included in the reminder, they will only be required to provide one level of authentication. By default, this level of authentication is a security answer set by the patient on their initial login. Accessing the patient portal through an institution link (and not through an email invitation) will require the patient to provide two levels of authentication, e.g., patient name, date of birth, last four digits of social security number or patient identifier, security answers, which are set by the patient upon initial login, and so forth. Within the portal, the patient can complete all pending questionnaires and review any questionnaires they have previously completed. As previously described, system 108 is configured to capture implant data, e.g., via a barcode scan and/or via manual entry.

System 108 implements various operations for accessing registry data. In an example, the access of information is based on various types of permissions. One type of permissions is across institutions/groups. In this example, data shared across institutions/groups will be de-identified, e.g., by removing social security number information, date of birth information, and so forth. Administrators of the registry have to option to enable identified views of the data across institutions/groups with the express permission of each participating institution/group.

Another permission type if within an institution/group. In this example, data between physician participants will remain de-identified, as with the data across institution. Administrators of the registry within the institution have the option to see identified data.

System 108 also includes a data mining module. The data mining module offers real-time access to data submitted to the registry with statistical functions and the ability to export filtered data to a CSV file (typically used within excel, SPSS, or SAS). The data mining module supports filtering by physician (if enabled in the registry permissions), PRO, patient demographics (age, gender, BMI, comorbidities, ICD-9 code, or CPT code). Trends are shown through a graph. Patient privacy is incorporated into the graphs, e.g., as physicians can see protected health information (PHI) identifiers for their own patients only. All data mined from the registry database is de-identified. In an example, the graph includes PRO score, and time interval at which the form was filled (in relation to the surgical encounter). In this example, the standard deviation automatically is calculated and displayed. The mean and correlation is automatically calculated.

Additionally, trends are also shown through a table, in which system 108 ensures patient privacy by enabling physicians to see PHI identifiers for their own patients only. Data mined from the registry database is de-identified. In some example, the table displays patient name, PRO score at each time interval (in relation to the surgical encounter), surgery date, gender, age, physician, and institution/group. Through the data mining tool, users have the ability to see individual responses to PROs. System 108 also supports keyword searching and exporting to a data file.

System 108 also includes an export module for real-time access to data points through a file export. Through the export module, a user can select to export data by PRO or physician-filled form and can select specific question items to be exported. Participating physicians can export their own data with patient identifiers, but other data remains de-identified.

System 108 also includes a predictive module that uses statistical methods to predict, or forecast, which patients are the greatest risks for a certain outcome, such as readmission, based on data collected.

Figure 5:
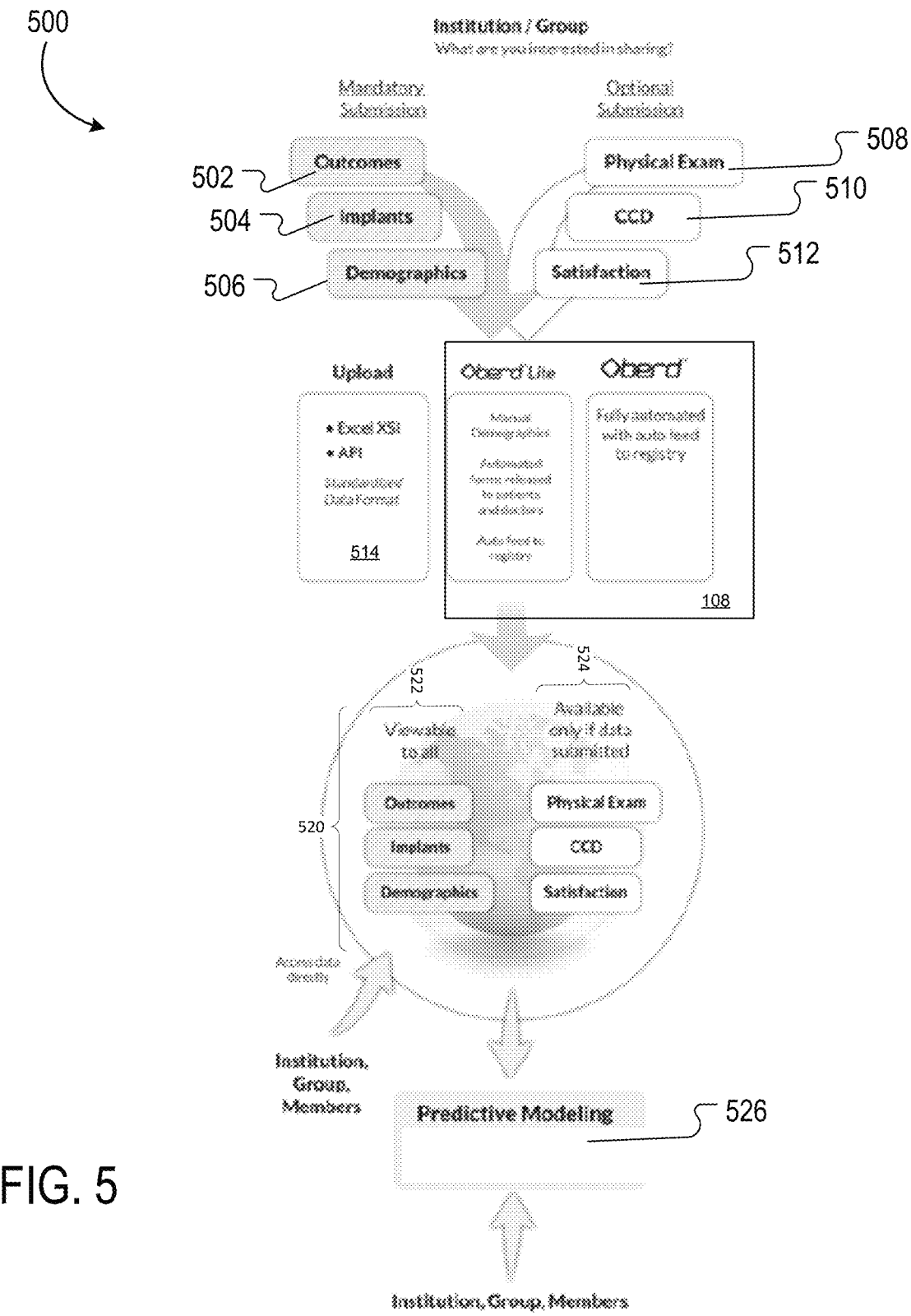

Referring to FIG. 5, diagram 500 displays a framework for another medical registry. In this example, submission of implants data 504, outcomes data 502, and demographics data 506 remain required for participation; however, participants can opt to submit data from standardized physical exams 508, Continuity of Care Document (CCD) data 510, and patient satisfaction data 512.

In this example, the medical registry 520 receives the medical data (e.g., both mandatory and optional) from various (external) sources. In one example, medical registry 520 receives the information from system 108, e.g., when users use system 108 to access and to view the forms and to submit answers. Medical registry 510 can also receive the registry data from an external system 514, e.g., when the data is uploaded into system 108 and the registry.

In this example, medical registry 512 includes area 522 for storage of information that is viewable to all users and area 524 for storage of information that is only viewable if users have submitted the same type of data. Based on the information in medical registry 520, system 108 includes a predictive modeling component 526 to perform predictive modeling of the information in the medical registry.

A participant who submits optional data will have access to the aggregate registry data within this area. For example, submitting satisfaction data provides the participant with access to all de-identified patient satisfaction within the registry. Conversely, participants who submit only the required data will be limited to mining data from these areas only.

In this example, administrators determine data fields that can be included in the registry. Participation is limited to licensed users. Physicians can request to participate through a public website and can submit their collected data through Excel XSI or through an established application programming interface (API). Participants have real-time access to the de-identified database through the data mining module, export module, and predictive modeling. In an example, only users submitting the optional data fields will be able to see the collected optional data. Additionally, system 108 implements a public site to allow prospective participants the ability to request to join the registry. This medical registry supports import of standardized data through an API with other outcomes, implants, satisfaction, tracking software, and so forth.

To participate in this medical registry, system 108 allows licensed (registered) users and unlicensed users. Data can be uploaded to registry through an API. The system 108 can virtually support an import of data from any system, provided that the minimum data standards (as set by system 108) are satisfied.

System 108 implements various techniques in setting up this type of registry, e.g., including the functionality previously described. In this example, a registry board determines and sends to system 108 data indicative of which optional submission features they want to collect (Standardized Physical Exam, CCD, Satisfaction). System 108 also receives information indicative of standardized physical exam. A registry board decides which elements to collect. A board can create their own exam form, or use elements from the physician-report part of an outcome form. System 108 also receives information specifying which elements from the CCD to collect.

Regarding patient satisfaction, system 108 uses its generated satisfaction form, a standardized form, such as CGCHAPS, and/or can generate specific questions for which answers are collected (e.g., from questions that are asked on most satisfaction forms)/For example, the question "how friendly was your physician" is asked on most satisfaction forms. When participants join the registry, they select what optional data and forms they will also submit. Participants will be able to change their submission options.

For this type of medical registry, system 108 implements data collection, e.g., using the previously described techniques. System 108 collects information indicative of a standardized physical exam. These exams will be filled by physicians during a patient visit by using a medical note. System 108 collects CCD data via an integration with the EMR. System 108 also collects CCD data via an API of an EMR. System 108 collects patient satisfaction data via the previously described operations. Forms are automatically released to patients at specified times, and patients will receive email reminders to increase compliance. Patients can fill the form online through the patient portal.

Registry data is accessed based on types of permissions, e.g., as previously described. Additionally, not all data is viewable to all members. Optionally submitted data will be restricted to be viewed only by members of the registry who submit that optional data. For example, members who submit only the required information will only see the required information. Members who submit satisfaction information, but not CCD information, will be able to see satisfaction and required information, but not CCD information.

Figure 6:
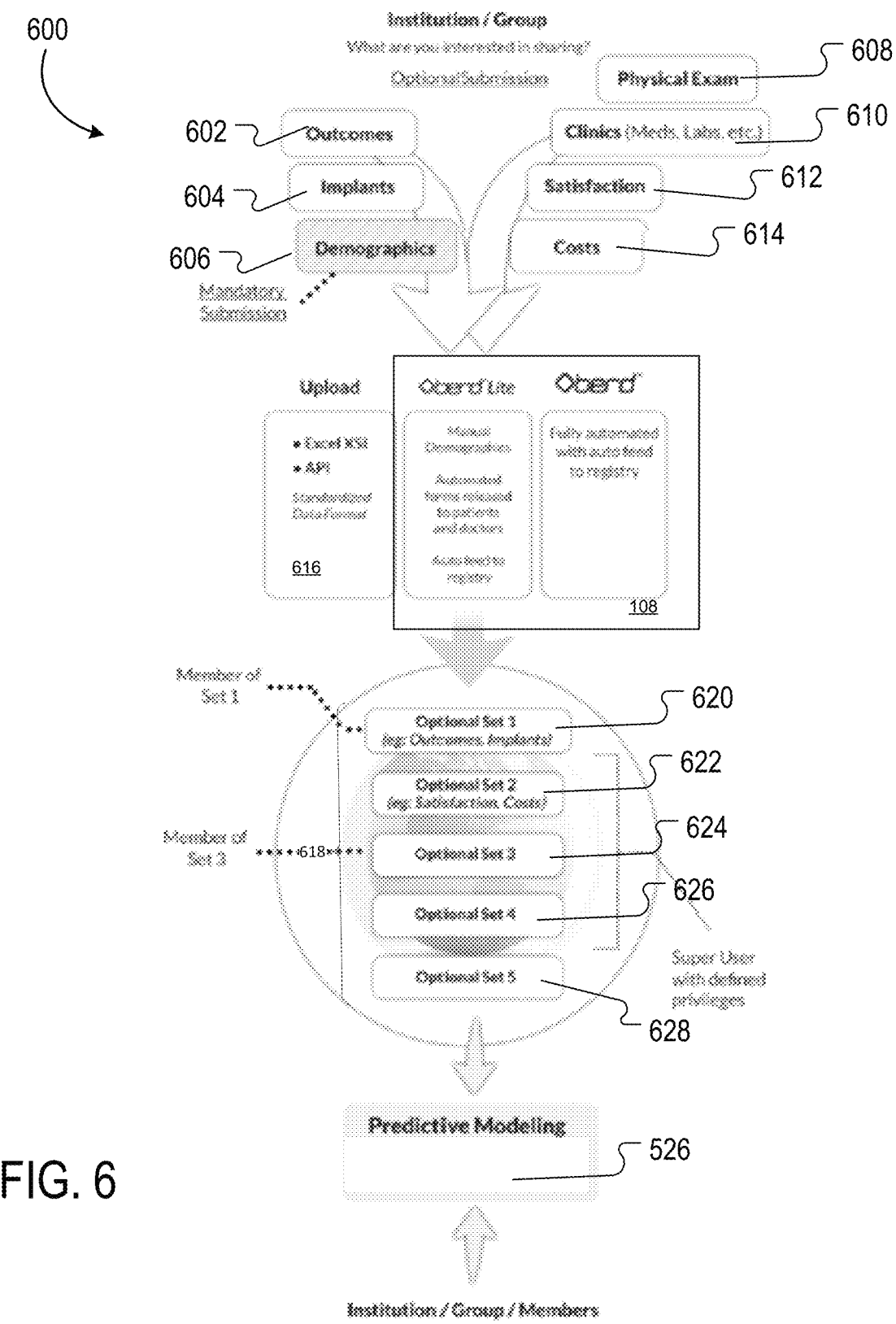

Referring to FIG. 6, diagram 600 displays a framework for another medical registry. In this example, the only mandatory submission is demographics data 606. Outcomes data 602 and implants data 604 are submitted on an optional basis and the ability to collect cost data 614 is added. Other optional data submissions include physical exam data 608, clinics data 610, satisfaction data 612, and costs data 614. Medical registry 618 receives the data from various sources, including, e.g., system 108 and external source 616 that uploads the data into system 108.

This registry 618 also implements a policy that participants can only see data within the categories they submit. By doing so, system 109 generates multiple registry sets, or sub-registries 620, 622, 624, 626, 628, within the global (e.g., main) registry database. Generally, a sub-registry includes a portion of a data repository that is dedicated to the storage of a particular type of information. There are various types of sub-registries, including, e.g., a sub-registry for orthopedics and a sub-registry for cardiology and so forth.

For example, sub-registry 620 includes outcome and implant data, in conjunction with the required demographics. The data a participant chooses to submit determines which sub-registry they will be able to see. System 108 defines "super users," with defined privileges that allow them to mine data from the entire registry regardless of their data submission, thus seeing the de-identified data from all sub-registries.

For example, the medical registry is a multi-registry of sorts, where "sub-registries" are included within an all-encompassing, or blanket (master) registry (e.g., master medical registry 114). In this example, only demographics data is a mandatory requirement to participate, thus increasing registry flexibility. Thus, outcomes and implants become optional submissions. Costs and clinics (Meds, Labs, etc.) are optionally fed into the registry as well.

The structure of the registry includes multiple "sub-registries" within a blanket registry. Each sub-registry collects different sets of data categories. For example, one sub-registry may collect specified outcomes and implants, while a second sub-registry may collect implants, satisfaction, and costs. Participants only see the data for the sub-registry they participate in. "Super Users," with defined privileges, will be able to mine data from the blanket registry, thus seeing the data from all sub-registries. In order to join a given sub-registry, the participant must submit all data being collected in that sub-registry.

In an example, a registry board determines which data will be collected within optional categories and submits information indicative of this determination to system 108. Sub-registries are automatically generated by system 108 based on which data participants submit. Only users who submit optional data will be able to mine/export the optional data they submit. Super users will have access the blanket registry which means they will have access to all the sub-registries data. All data will be de-identified for super users.

In an example, the medical registries and system described herein improve the functionality of a computer, e.g., by removing PRO data and other received data that is not used and stored in the medical registry, e.g., thereby limiting the amount of data that is required for processing and updating of a medical registry.

Figure 7:
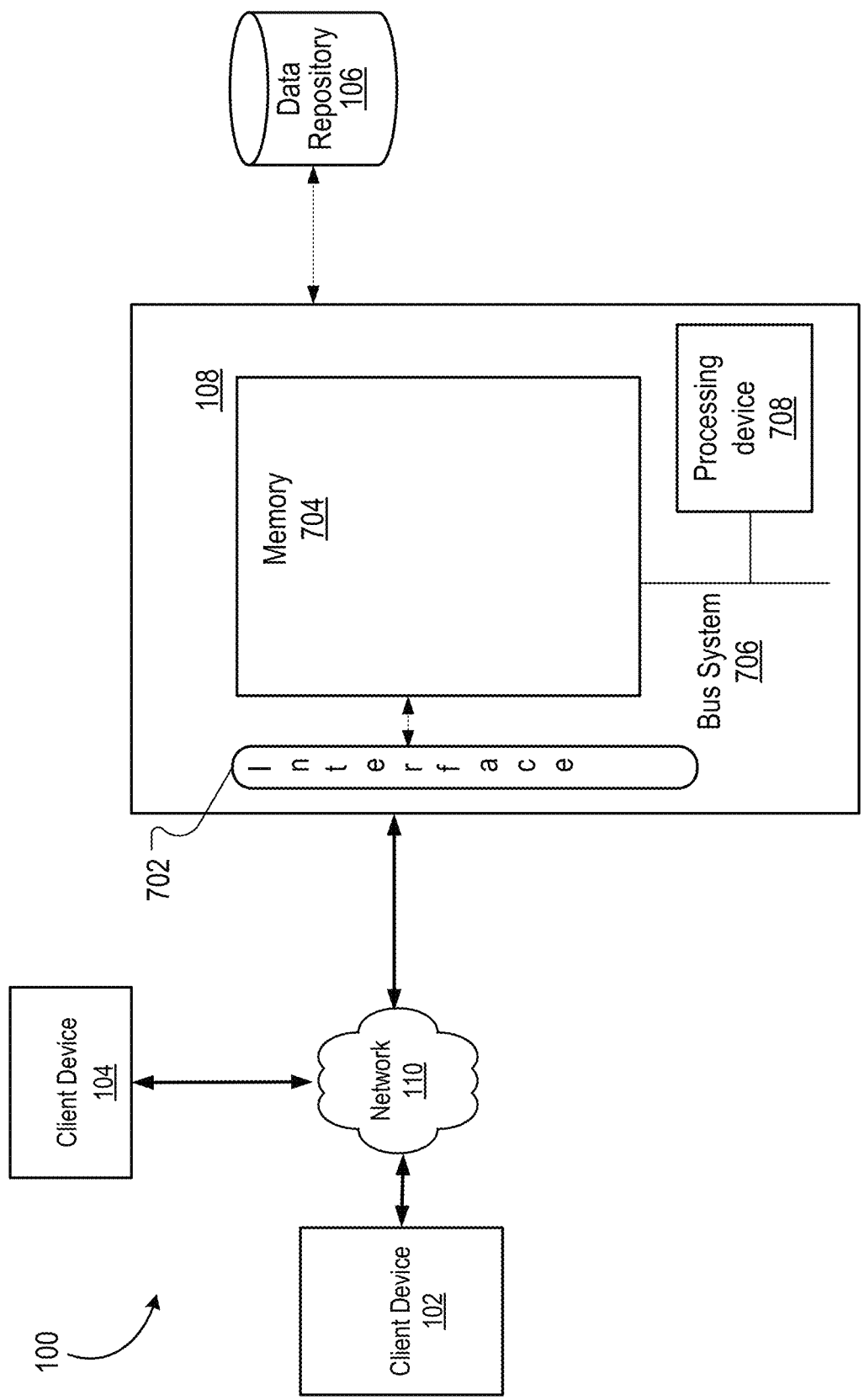
FIG. 7 is a diagram of components of the system that implements a medical registry.

FIG. 7 is a block diagram of components of networked environment 100. Client devices 102, 104 can be any sort of computing device capable of taking input from a user and communicating over a network with system 108 and/or with other client devices. Each of client devices 102, 104 can be a mobile device, a desktop computer, a laptop, a cell phone, a personal digital assistant ("PDA"), a server, an embedded computing system, a mobile device and so forth.

System 108 can be any of a variety of computing devices capable of receiving information, such as a server, a distributed computing system, a desktop computer, a laptop, a cell phone, a rack-mounted server, and so forth. System 108 may be a single server or a group of servers that are at a same location or at different locations.

System 108 can receive information from one or more of client devices 102, 104 via interface 702. Interface 702 can be any type of interface capable of receiving information over a network, such as an Ethernet interface, a wireless networking interface, a fiber-optic networking interface, a modem, and so forth. System 108 also includes a processing device 708 and memory 704. A bus system 706, including, for example, a data bus and a motherboard, can be used to establish and to control data communication between the components of system 108. Processing device 708 may include one or more microprocessors. Generally, processing device 708 may include any appropriate processor and/or logic that is capable of receiving and storing data, and of communicating over a network (not shown). Memory 704 can include a hard drive and a random access memory storage device, such as a dynamic random access memory, machine-readable media, or other types of non-transitory machine-readable storage devices.

Figure 8:
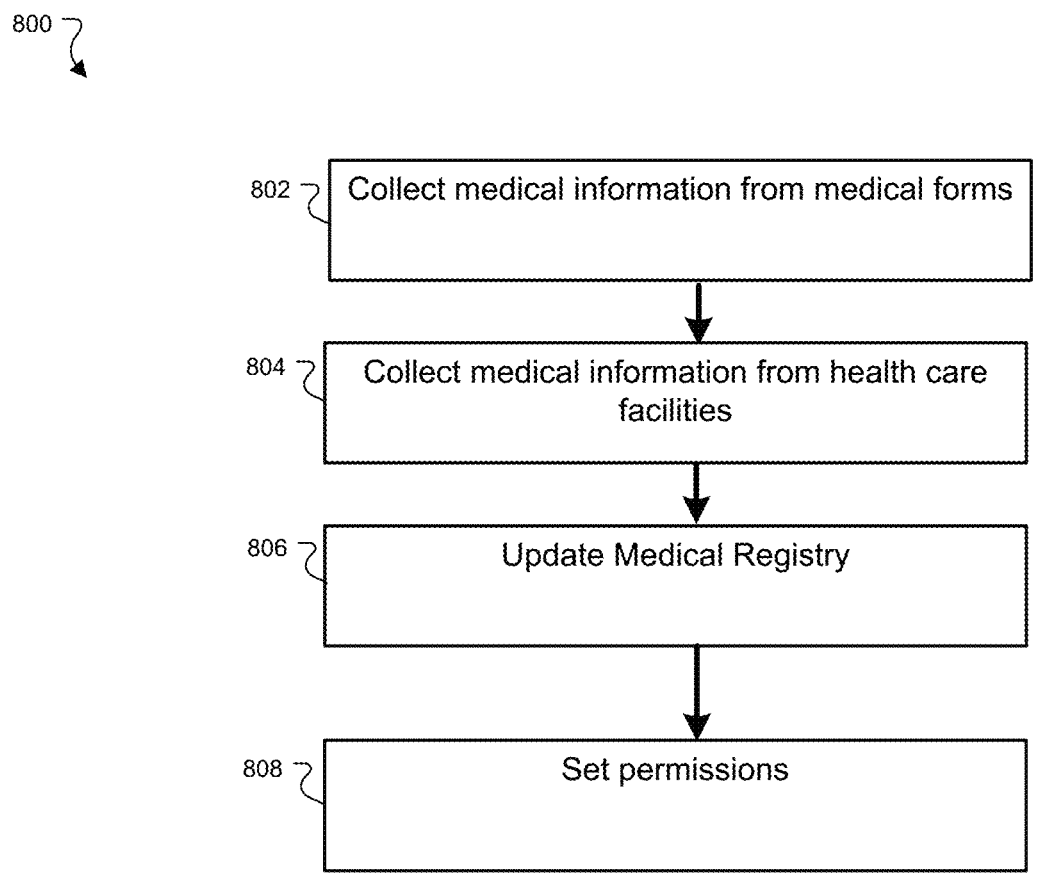
FIG. 8 is a flow chart of a process for updating a medical registry.

Referring to FIG. 8, system 108 performs process 800 in updating a medical registry. In operation, system 108 collects (802) medical information from a plurality of medical forms. As described herein, system 108 can be configured to have an autofeed from another system that implements and manages the medical forms. In another example, a user may upload the answers from the various medical forms to system 108. System 108 also collects (804) medical information from various medical facilities, e.g., from computer systems that are implemented by various hospitals or other health care facilities. As described herein, there are various types of collected medical information, including, e.g., demographic information, outcomes information, implants information, physical examination information, satisfaction information, and so forth.

Next, system 108 updates (806) a medical registry with the collected medical information, e.g., by updating various portions of the medical registry with relevant information. For example, the collected information may be tagged with identifying information (e.g., a tag that specifies that the information is outcome information). In this example, the various areas of the medical registry are also tagged (e.g., with information that specifies that an area is for medical outcome information). System 108 updates the appropriate portion of the medical registry with the collected information that is pertinent to that area.

System 108 also sets (808) permissions, e.g., such that users can only access those portions of the registry to which they have contributed. To do so, system 108 stores information indicative of an identity of a user who submitted the answers. For example, system 108 receives information specifying a set of answers and a username or numerical identifier (ID) for the user who submitted the answers. System 108 stores this identifying information in association with other information that specifies the type of medical information that is submitted and/or the type of registry to which the user's information is stored (and thus the type of registry to which the user contributed information). System 108 then uses this stored information in determining whether a user should be granted access to a registry or a sub-registry.

For example, system 108 receives, from a client device, a request to access information in one of the sub-registries. System 108 determines a type of medical information stored in the requested sub-registry and determines determine whether a user associated the client device has contributed to the requested sub-registry the determined type of medical information (by determining whether an ID for the user is associated with a registry of the requested type). When the user has not contributed to the requested sub-registry the determined type of medical information, system denies access to the sub-registry. When the user has contributed to the requested sub-registry the determined type of medical information, system 108 grants access to the sub-registry.

For example, a permission may be set that specifies that only users who have contributed to outcome data may view and/or search other outcomes data. In an example, a user may be an individual person or an entire health care facility. For example, an individual person may not search medical outcome data, unless that person has individually contributed medical outcomes data to the medical registry. In another example, an individual person may not search medical outcome data, unless that the individual or a hospital associated with the individual has contributed medical outcomes data to the medical registry.

Figure 9:
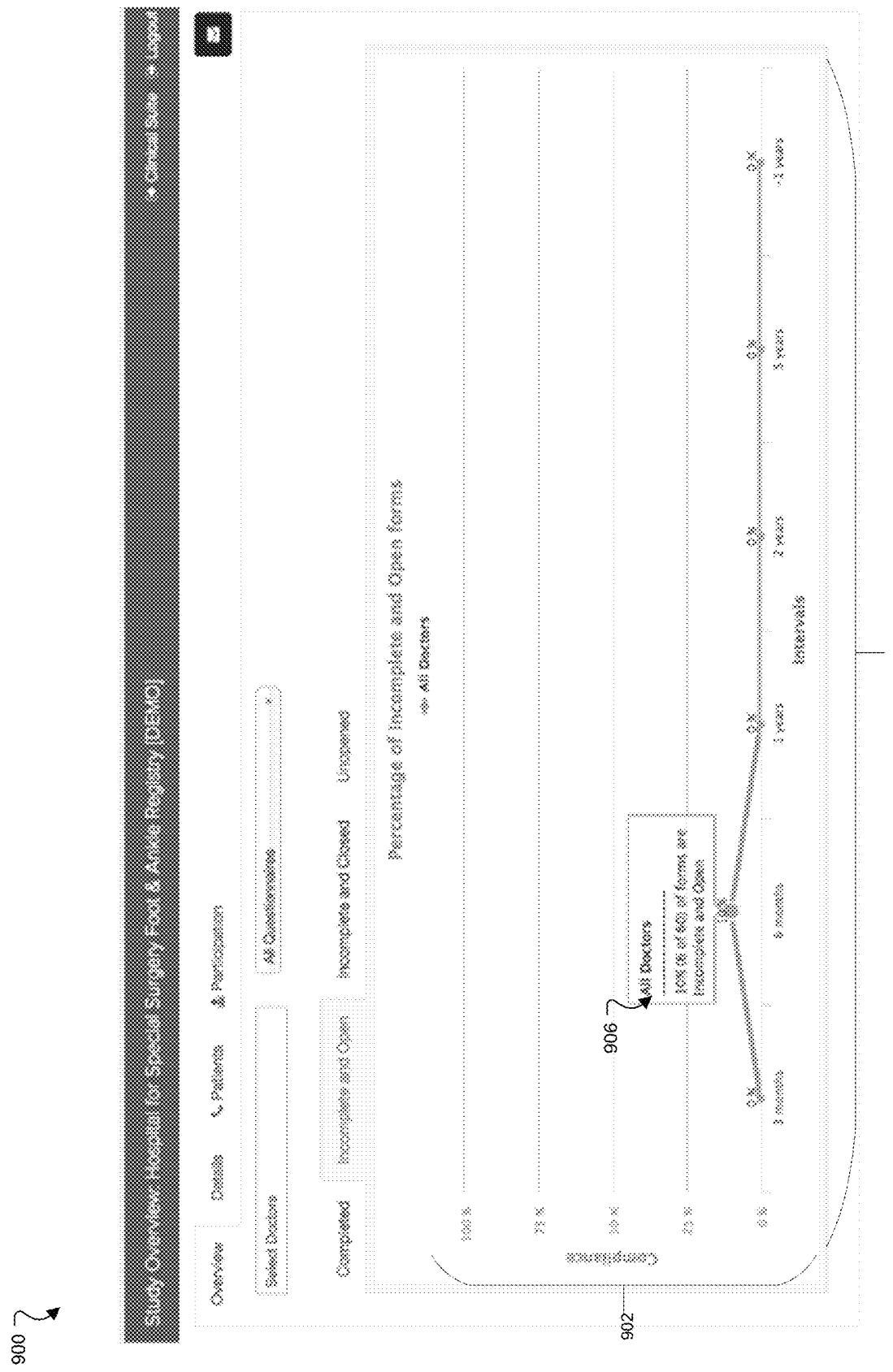
FIG. 9 is an example graphical user interface of that displays the tracking of compliance metrics.

Referring to FIG. 9, graphical user interface 900 displays compliance information for monitoring a study. In this example, graphical user interface 900 shows compliance for a particular hospital. In another example, graphical user interface 900 could show compliance for a particular practice area of a hospital (e.g., foot surgery). In the example shown in FIG. 9, a specialized area of the hospital how its own registry. Because of the auto-feed from the system or database that manages the medical forms to the medical registry, a system that implements the medical registry is able to very easily track which forms have been submitted for patient completion, which submitted forms are actually completed and a percentage of compliance. In this example, compliance refers to a number or percentage of forms that have been completed.

In an example, when a patient first enters a medical facility, the registry is updated with the patient's information (e.g., name information, demographics information, and so forth). In this example, system 108 associates various forms with the patient. The medical registry (and/or system 108) tracks when the forms have been sent to the patient, when the patient has worked on a form, when a patient has been sent a reminder to complete the form, and when a form is completed. The medical registry is updated with this tracked information (e.g., and associated with the patient record). Using this tracked information, system 108 determines compliance. As shown in FIG. 9, compliance metrics 902 are tracked over various time intervals 904. Graphical user interface 900 also includes portion 906 (e.g., a dot on the graph) that when selected sends a patient an electronic reminder to complete the form.

Figure 10:
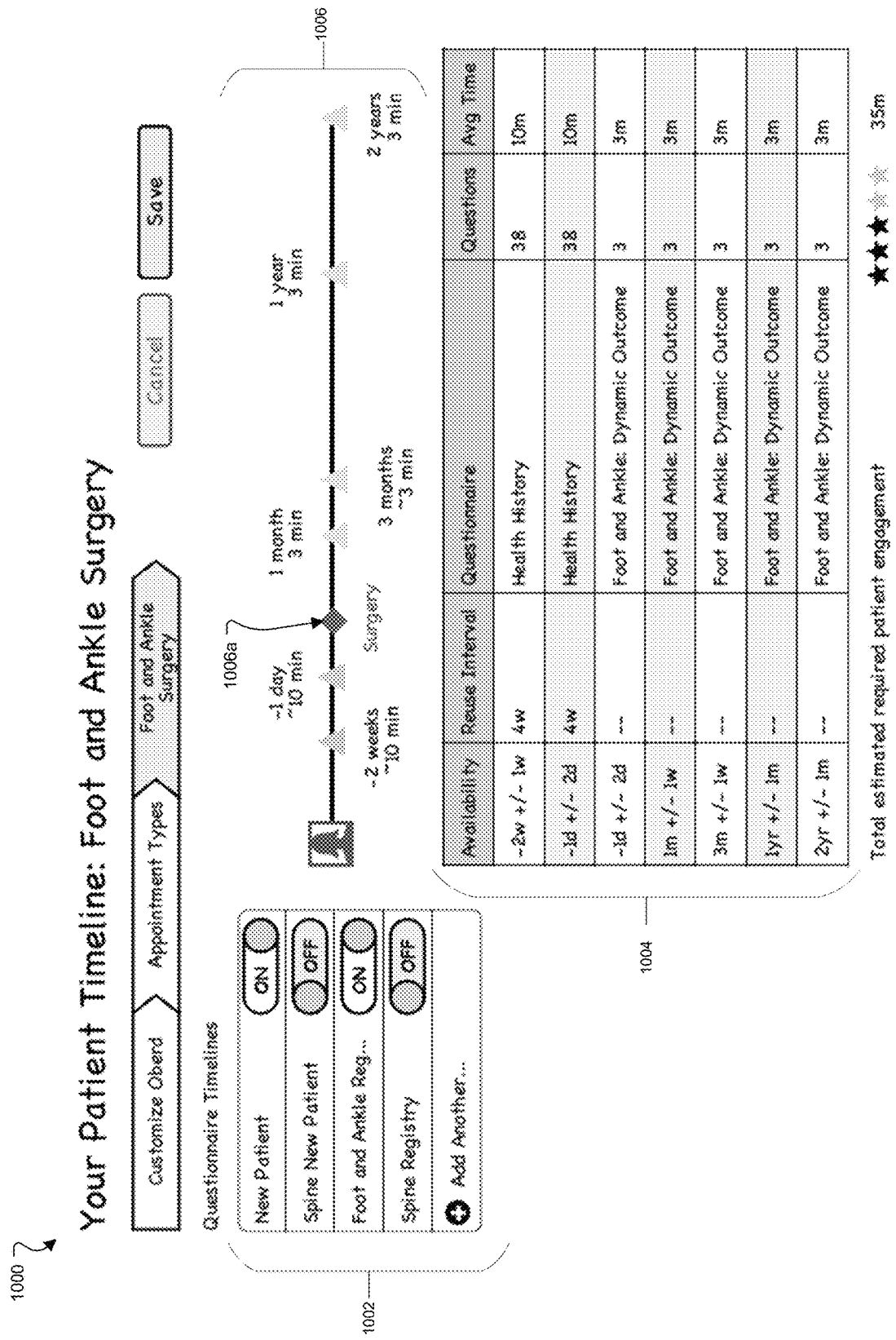
FIG. 10 is an example graphical user interface to balance the number of questions asked vs. registry compliance.

Referring to FIG. 10, graphical user interface 1000 enables a user balance the number of questions asked vs. registry compliance. Graphical user interface 1000 includes portion 1002 for a user to select which questionnaires are sent to a patient. Graphical user interface 1000 also includes portion 1004 that specifies in an availability column when the questions needs to be completed (e.g., a range of dates), how often the questions can be reused, a number of questions, and the average time that is takes to complete the questions. Graphical user interface 1000 also includes time-line portion 1006 that specifies when a patient is completing patient questionnaires relative to a surgery date that is specified by date 1006a.

As used herein, the terms "computer" and "computer systems" refer broadly to any sort of combination of one or more servers and/or computing devices. As used herein, the terms "instrument(s)" and "medical study instrument(s)" refer broadly to any type of device and/or document (or any combination thereof), which presents data and/or information to a user and allows the user to input and/or send data and/or information to the system.

Embodiments can be implemented in digital electronic circuitry, or in computer hardware, firmware, software, or in combinations thereof. An apparatus can be implemented in a computer program product tangibly embodied or stored in a machine-readable storage device for execution by a programmable processor; and method actions can be performed by a programmable processor executing a program of instructions to perform functions by operating on input data and generating output. The embodiments described herein, and other embodiments of the invention, can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

To provide for interaction with a user, embodiments can be implemented on a computer having a display device, e.g., a LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments can be implemented in a computing system that includes a back end component, e.g., as a data server, or that includes a middleware component, e.g., an application server, or that includes a front end component, e.g., a client computer having a graphical user interface or a Web browser through which a user can interact with an implementation of embodiments, or any combination of such back end, middleware, or front end components. The components of the system can be interconnected by any form or medium of digital data communication, e.g., a communication network. Examples of communication networks include a local area network (LAN) and a wide area network (WAN), e.g., the Internet.

The system and method or parts thereof may use the "World Wide Web" (Web or WWW), which is that collection of servers on the Internet that utilize the Hypertext Transfer Protocol (HTTP). HTTP is a known application protocol that provides users access to resources, which may be information in different formats such as text, graphics, images, sound, video, Hypertext Markup Language (HTML), as well as programs. Upon specification of a link by the user, the client computer makes a TCP/IP request to a Web server and receives information, which may be another Web page that is formatted according to HTML. Users can also access other pages on the same or other servers by following instructions on the screen, entering certain data, or clicking on selected icons. It should be noted that any type of selection device known to those skilled in the art, such as check boxes, drop-down boxes, and the like, may be used for embodiments using web pages to allow a user to select options for a given component. Servers run on a variety of platforms, including UNIX machines, although other platforms, such as Windows 2000/2003, Windows NT, Sun, Linux, and Macintosh may also be used. Computer users can view information available on servers or networks on the Web through the use of browsing software, such as Firefox, Netscape Navigator, Microsoft Internet Explorer, or Mosaic browsers. The computing system can include clients and servers. A client and server are generally remote from each other and typically interact through a communication network. The relationship of client and server arises by virtue of computer programs running on the respective computers and having a client-server relationship to each other.

Other embodiments are within the scope and spirit of the description claims. Additionally, due to the nature of software, functions described above can be implemented using software, hardware, firmware, hardwiring, or combinations of any of these. Features implementing functions may also be physically located at various positions, including being distributed such that portions of functions are implemented at different physical locations. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the techniques described herein.

What is claimed is:

1. A computer-implemented method comprising:
  receiving, by a server system and from an automated feed of a practice management system, information indicative of patients of a medical facility associated with the practice management system;
  updating, by the server system comprising at least one processor having access to a network, a plurality of medical registries with the information indicative of the patients;
  assigning by the server system a plurality of medical forms to the patients;
  transmitting the assigned medical forms to client devices of the patients;
  receiving, by the server system and from the automated feed of the practice management system, data structures that include fields structuring data that represents answers to questions included in the medical forms, wherein the data includes a first answer including medical information of a first type submitted by a user;
  filtering values in the fields of the data structure representing the received answers to determine, for each of the received answers, one or more medical registries of the plurality of medical registries that are to be updated based on content of the received answers, wherein the one or more medical registries include a first medical registry for storing the first type of medical information, wherein filtering the values in the fields of the data structure representing the received answers to determine, for each of the received answers, the one or more medical registries that are to be updated based on the content of the received answers comprises correlating data representing answers to the questions that is included in the fields of the received data structures with data structured by one or more fields of other data structures stored in a memory device that represent respective subject matter designations that each correspond to medical information stored in a respective medical registry;
  storing, by the server system, the filtered answers in one or more fields of data structures stored in a memory devices that are used to structure data representing the one or more medical registries, wherein storing the filtered answers comprises determining the first answer is correlated with a subject matter designation that corresponds to the first medical registry and storing the medical information of the first type submitted by the user in the first medical registry of the one or more medical registries; and
  subsequent to storing the filtered answers in the one or more fields of the data structures stored in the memory device that are used to structure data representing the one or more medical registries:
    receiving, from a client device of the user, a request to access information in the first medical registry that stores the first type of medical information;
    determining that the user associated with the request has contributed the medical information of the first type stored in the first medical registry to the first medical registry; and
    based on a determination that the user has contributed the medical information of the first type stored in the first medical registry to the first medical registry, providing access, to other information of the first type stored in the first medical registry, to the user.

2. The computer-implemented method of claim 1, wherein a registry of the plurality of medical registries is an orthopedics registry, and a second registry of the plurality of medical registries is a cardiology registry.

3. The computer-implemented method of claim 1, further comprising:
  storing information indicative of an identity of the user who submitted the first answer.

4. The computer-implemented method of claim 1, further comprising:
    automatically scoring multiple patient-reporting outcomes with a condensed version of a medical form, based on the answers that are received via the automated feed.

5. The computer-implemented method of claim 1, wherein the method further comprising:
    tracking, based on the one or more medical registries storing the filtered data records, a level of completion of the assigned medical forms based on an evaluation of one or more compliance metrics.

6. The computer-implemented method of claim 1, wherein the method further comprising:
    based on a determination that the user has not contributed to the first medical registry, denying access to the first medical registry by the user.

7. One or more machine-readable hardware storage devices storing instructions that are executable by one or more processing devices to perform operations comprising:
    receiving, by a server system and from an automated feed of a practice management system, information indicative of patients of a medical facility associated with the practice management system;
    updating, by the server system comprising at least one processor having access to a network, a plurality of medical registries with the information indicative of the patients;
    assigning by the server system a plurality of medical forms to the patients;
    transmitting the assigned medical forms to client devices of the patients;
    receiving, by the server system and from the automated feed of the practice management system, data structures that include fields structuring data that represents answers to questions included in the medical forms, wherein the data includes a first answer including medical information of a first type submitted by a user;
    filtering values in the fields of the data structure representing the received answers to determine, for each of the received answers, one or more medical registries of the plurality of medical registries that are to be updated based on content of the received answers, wherein the one or more medical registries include a first medical registry for storing the first type of medical information, wherein filtering the values in the fields of the data structure representing the received answers to determine, for each of the received answers, the one or more medical registries that are to be updated based on the content of the received answers comprises correlating data representing answers to the questions that is included in the fields of the received data structures with data structured by one or more fields of other data structures stored in a memory device that represent respective subject matter designations that each correspond to medical information stored in a respective medical registry;
    storing, by the server system, the filtered answers in one or more fields of data structures stored in a memory devices that are used to structure data representing the one or more medical registries, wherein storing the filtered answers comprises determining the first answer is correlated with a subject matter designation that corresponds to the first medical registry and storing the medical information of the first type submitted by the user in the first medical registry of the one or more medical registries; and
    subsequent to storing the filtered answers in the one or more fields of the data structures stored in the memory device that are used to structure data representing the one or more medical registries:
        receiving, from a client device of the user, a request to access information in the first medical registry that stores the first type of medical information;
        determining that the user associated with the request has contributed the medical information of the first type stored in the first medical registry to the first medical registry; and
        based on a determination that the user has contributed the medical information of the first type stored in the first medical registry to the first medical registry, providing access, to other information of the first type stored in the first medical registry, to the user.

8. The one or more machine-readable hardware storage devices of claim 7, wherein a registry of the plurality of medical registries is an orthopedics registry, and a second registry of the plurality of medical registries is a cardiology registry.

9. The one or more machine-readable hardware storage devices of claim 7, wherein the operations further comprise:
    storing information indicative of an identity of the user who submitted the first answer.

10. The one or more machine-readable hardware storage devices of claim 7, wherein the operations further comprise:
    automatically scoring multiple patient-reporting outcomes with a condensed version of a medical form, based on the answers that are received via the automated feed.

11. The one or more machine-readable hardware storage devices of claim 7, wherein the operations further comprising:
    tracking, based on the one or more medical registries storing the filtered data records, a level of completion of the assigned medical forms based on an evaluation of one or more compliance metrics.

12. The one or more machine-readable hardware storage devices of claim 7, wherein the operations further comprising:
    based on a determination that the user has not contributed to the first medical registry, denying access to the first medical registry by the user.

13. An electronic system comprising:
    one or more processing devices; and
    one or more machine-readable hardware storage devices storing instructions that are executable by one or more processing devices to perform operations comprising:
    receiving, by a server system and from an automated feed of a practice management system, information indicative of patients of a medical facility associated with the practice management system;
    updating, by the server system comprising at least one processor having access to a network, a plurality of medical registries with the information indicative of the patients;
    assigning by the server system a plurality of medical forms to the patients;
    transmitting the assigned medical forms to client devices of the patients;
    receiving, by the server system and from the automated feed of the practice management system, data structures that include fields structuring data that represents answers to questions included in the medical forms, wherein the data includes a first answer including medical information of a first type submitted by a user;

filtering values in the fields of the data structure representing the received answers to determine, for each of the received answers, one or more medical registries of the plurality of medical registries that are to be updated based on content of the received answers, wherein the one or more medical registries include a first medical registry for storing the first type of medical information, wherein filtering the values in the fields of the data structure representing the received answers to determine, for each of the received answers, the one or more medical registries that are to be updated based on the content of the received answers comprises correlating data representing answers to the questions that is included in the fields of the received data structures with data structured by one or more fields of other data structures stored in a memory device that represent respective subject matter designations that each correspond to medical information stored in a respective medical registry;

storing, by the server system, the filtered answers in one or more fields of data structures stored in a memory devices that are used to structure data representing the one or more medical registries, wherein storing the filtered answers comprises determining the first answer is correlated with a subject matter designation that corresponds to the first particular medical registry and storing the medical information of the first type submitted by the user in the first medical registry of the one or more medical registries; and subsequent to storing the filtered answers in the one or more fields of the data structures stored in the memory device that are used to structure data representing the one or more medical registries:

receiving, from a client device of the user, a request to access information in the first medical registry that stores the first type of medical information;

determining that the user associated with the request has contributed the medical information of the first type stored in the first medical registry to the first medical registry; and based on a determination that the user has contributed the medical information of the first type stored in the first medical registry to the first medical registry, providing access, to other information of the first type stored in the first medical registry, to the user.

14. The electronic system of claim 13, wherein a registry of the plurality of medical registries is an orthopedics registry, and a second registry of the plurality of medical registries is a cardiology registry.

15. The electronic system of claim 13, wherein the operations further comprise:

storing information indicative of an identity of the user who submitted the first answer.

16. The electronic system of claim 13, wherein the operations further comprise:

automatically scoring multiple patient reporting outcomes with a condensed version of a medical form, based on the answers that are received via the automated feed.

17. The electronic system of claim 13, wherein the operations further comprising:

tracking, based on the one or more medical registries storing the filtered data records, a level of completion of the assigned medical forms based on an evaluation of one or more compliance metrics.

18. The electronic system of claim 13, wherein the operations further comprising:

based on a determination that the user has not contributed to the first medical registry, denying access to the first medical registry by the user.

* * * * *